United States Patent
Lee et al.

(10) Patent No.: US 11,425,509 B2
(45) Date of Patent: Aug. 23, 2022

(54) ATMOSPHERIC PRESSURE ADJUSTMENT APPARATUS AND ATMOSPHERIC PRESSURE ADJUSTMENT METHOD OF ATMOSPHERIC PRESSURE ADJUSTMENT APPARATUS

(71) Applicant: SAMSUNG ELECTRONICS CO., LTD., Suwon-si (KR)

(72) Inventors: Jong Hwa Lee, Suwon-si (KR); Yang Wook Kim, Suwon-si (KR); Chang Han Kim, Suwon-si (KR); Gui Won Seo, Suwon-si (KR); Sung Won Cho, Suwon-si (KR); Jin Ho Park, Suwon-si (KR); Hyeong Cheol Jeong, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 94 days.

(21) Appl. No.: 16/763,342

(22) PCT Filed: Nov. 5, 2018

(86) PCT No.: PCT/KR2018/013322
§ 371 (c)(1),
(2) Date: May 12, 2020

(87) PCT Pub. No.: WO2019/103352
PCT Pub. Date: May 31, 2019

(65) Prior Publication Data
US 2020/0336843 A1    Oct. 22, 2020

(30) Foreign Application Priority Data
Nov. 21, 2017  (KR) .......................... 10-2017-0155889

(51) Int. Cl.
*H04R 25/00*  (2006.01)
*A61F 11/08*  (2006.01)
*G01L 27/00*  (2006.01)

(52) U.S. Cl.
CPC .............. *H04R 25/30* (2013.01); *A61F 11/08* (2013.01); *G01L 27/002* (2013.01); *H04R 2460/05* (2013.01)

(58) Field of Classification Search
CPC . A61F 11/08; H04R 2460/11; H04R 2460/17; H04R 25/656
(Continued)

(56) References Cited

U.S. PATENT DOCUMENTS 8,187,202 B2    5/2012  Akkermans et al.
8,229,145 B2    7/2012  Coughlan et al.
(Continued)

FOREIGN PATENT DOCUMENTS

JP    6-335473    12/1994
JP    3765981    4/2006
(Continued)

OTHER PUBLICATIONS

International Search Report (with English translation), for PCT/KR2018/013322, dated Feb. 12, 2019, 4 pages.
(Continued)

*Primary Examiner* — George C Monikang
(74) *Attorney, Agent, or Firm* — Nixon & Vanderhye, P.C.

(57) ABSTRACT

An atmospheric pressure adjustment apparatus is disclosed. The atmospheric pressure adjustment apparatus comprises: a speaker; a microphone; an earplug of which a main body is made of an elastic material so as to seal the external auditory meatus when the earplug is worn on the ear of a user, and which comprises an atmospheric pressure adjustment part
(Continued)

penetrating the main body; and atmospheric pressure adjustment device for adjusting the fluid volume of the atmospheric pressure adjustment part; and a processor for outputting a sound through the speaker when the earplug is worn, measuring the air pressure difference between the middle ear internal atmospheric pressure and the external auditory meatus atmospheric pressure of the user on the basis of the strength of a received echo when the echo of the sound reflected from the eardrum of the user is received through the microphone, and adjusting the atmospheric pressure difference by moving the atmospheric pressure adjustment device according to the measured atmospheric pressure difference.

13 Claims, 13 Drawing Sheets

(58) Field of Classification Search
USPC ........................................ 381/312, 328, 71.5
See application file for complete search history.

(56) References Cited

U.S. PATENT DOCUMENTS

| | | | |
|---|---|---|---|
| 9,002,023 | B2 | 4/2015 | Gauger, Jr. |
| 9,402,140 | B2 | 7/2016 | Kim |
| 10,251,790 | B2 | 4/2019 | George et al. |
| 2004/0163882 | A1* | 8/2004 | Fleming .................. A61F 11/10 181/135 |
| 2014/0044159 | A1 | 2/2014 | Poulton et al. |
| 2014/0044574 | A1 | 2/2014 | Iitsuka et al. |
| 2015/0003644 | A1 | 1/2015 | George et al. |

FOREIGN PATENT DOCUMENTS

| | | |
|---|---|---|
| JP | 2007-282907 | 11/2007 |
| JP | 2009-065669 | 3/2009 |
| KR | 10-2010-0112372 | 10/2010 |
| KR | 10-1025786 | 4/2011 |
| KR | 10-2015-0038855 | 4/2015 |
| KR | 10-1535112 | 7/2015 |
| KR | 10-1558091 | 10/2015 |
| KR | 10-2016-0027003 | 3/2016 |
| KR | 10-2016-0027013 | 3/2016 |
| KR | 10-1685691 | 12/2016 |
| KR | 10-1778065 | 9/2017 |

OTHER PUBLICATIONS

Written Opinion of the ISA (with English Translation) for PCT/KR2018/013322, dated Feb. 12, 2019, 13 pages.

Eaton, Kit, "Ear Pressure Equalizer Sucks on Your Eardrum to Un-Pop It in Planes," Oct. 28, 2008, 1 page (https://gizmodo.com/5069686/ear-pressure-equalizer-sucks-on-your-eardrum-to-un-pop-it-in-planes).

Notice of Preliminary Rejection dated May 27, 2022 in KR Application No. 10-2017-0155889 and English-language translation.

* cited by examiner (a)

(b)

(c)

(a)

(b)

(c)

ATMOSPHERIC PRESSURE ADJUSTMENT APPARATUS AND ATMOSPHERIC PRESSURE ADJUSTMENT METHOD OF ATMOSPHERIC PRESSURE ADJUSTMENT APPARATUS

This application is the U.S. national phase of International Application No. PCT/KR2018/013322 filed 5 Nov. 2018, which designated the U.S. and claims priority to KR Patent Application No. 10-2017-0155889 filed 21 Nov. 2017, the entire contents of each of which are hereby incorporated by reference.

FIELD

This disclosure relates to an air pressure adjustment apparatus and an air pressure adjustment method of an air pressure adjustment apparatus. More specifically, the disclosure relates to an air pressure adjustment apparatus for adjusting an air pressure difference between an air pressure of an internal part of a middle ear and an air pressure of an external auditory meatus and an air pressure adjustment method of the air pressure adjustment apparatus.

DESCRIPTION OF RELATED ART

In a case where an air pressure suddenly changes, such as when an airplane takes off or lands, when going up or down a high mountain or a building, or when riding in a paragliding or high-speed elevator, or the like, a person may feel as if the ear is popping or feel pain in the ear, since a sudden change in air pressure causes an air pressure difference between internal pressure and external pressure of the middle ear, leading to eardrum swelling.

FIG. 1A illustrates a structure of a human ear. In FIG. 1A, reference numeral 1 denotes external auditory meatus, 2 denotes eardrum, 3 denotes an internal part of a middle ear, and 4 denotes the Eustachian tube. In a normal case, external air pressure, that is, the air pressure of the external auditory meatus 1 and the air pressure of the internal part of the middle ear 3 are in equilibrium, and as shown in FIG. 1B(a), the eardrum 2 is maintained in a flat state.

However, for example, when an airplane takes off, the air pressure of the external auditory meatus 1 is lowered, and at this time, unless a person makes an action such as yawning or swallowing, the Eustachian tube 4 connected to an outside through nose is kept closed. Accordingly, the difference between the air pressure of the internal part of the middle ear 3 and the air pressure of the external auditory meatus 1 occurs. Since the air pressure of the external auditory meatus 1 is lower than the air pressure of the internal part of the middle ear 3, the eardrum 2 expands in the direction of the external auditory meatus 1 as shown in FIG. 1B(b), and a person may feel the pain in the ear or feel as if the ear is popping. When an airplane is landing, on the contrary, an air pressure difference in the opposite direction is generated between the internal part of the middle ear 3 and the external auditory meatus 1, and as shown in FIG. 1B(c), the eardrum 2 is expanded, causing inconvenience to the person, in the same manner.

It is possible to make the air pressure of the external auditory meatus 1 and the air pressure of the internal part of the middle ear 3 in equilibrium through an action such as intentionally yawning and swallowing to open the Eustachian tube 4, but it is cumbersome to yawn or swallow continuously. If the Eustachian tube 4 is blocked due to otitis, sinus cold, rhinitis, or the like, feeling as if the ear is popping or feeling the pain in the ear may not be overcome even with swallowing or yawning. In order to address this problem, a medicine may be taken to dry nasal discharge or forcibly expand the Eustachian tube 4, but a person may be burdened with taking a medicine.

In the related art, there has been an earplug for air pressure adjustment which makes air pressure slowly change through a small hole or an external auditory meatus pressure adjustment device to adjust air pressure through a conduit by connecting an earphone conduit and a fluid flow device, without a necessity to take a medicine. However, in an environment in which the air pressure difference between the internal part of the middle ear 3 and the external auditory meatus 1 has been already generated, wearing the earplug or device is not meaningful, and the person needs to manually manipulate a pump to adjust the air pressure, thereby the causing inconvenience to the person.

SUMMARY

The disclosure is to address the above-described problems, and an object of the disclosure is to provide an air pressure adjustment apparatus capable of measuring the air pressure difference between the internal part of the middle ear and the external auditory meatus to automatically adjust the difference of air pressure, and an air pressure adjustment method of the air pressure adjustment apparatus.

According to an embodiment, an air pressure adjustment apparatus includes a speaker, a microphone, an earplug of which a main body is made of an elastic material so as to seal an external auditory meatus, based on the earplug being worn on an ear of a user, and which comprises an air pressure adjustment part penetrating the main body, n air pressure adjustment device configured to adjust a fluid volume of the air pressure adjustment part, and a processor configured to output a sound through the speaker based on the earplug being worn, measure the air pressure difference between air pressure of an internal part of the middle ear and air pressure of an external auditory meatus on the basis of strength of a received eco based on the echo of the sound reflected from the eardrum of the user being received through the microphone, and adjust the air pressure difference by moving the air pressure adjustment device according to the measured air pressure difference.

The air pressure adjustment apparatus may further include an air pressure sensor configured to sense the air pressure of the external auditory meatus, and the processor may, based on receiving the echo from the microphone, determine the air pressure of the internal part of the middle ear on the basis of data relating to the echo strength according to the air pressure of the internal part of the middle ear, and measure an air pressure difference between the air pressure of the internal part of the middle ear and the air pressure of the external auditory meatus of the user by sensing the air pressure of the external auditory meatus through the air pressure sensor.

The processor may calculate a change amount of the fluid volume of the air pressure adjustment part corresponding to the air pressure difference, and adjust the air pressure difference by moving the air pressure adjustment device so that the fluid volume of the air pressure adjustment part changes according to the calculated change amount.

The processor may, based on the middle ear internal air pressure being higher than the air pressure of the external auditory meatus, move the air pressure adjustment device so that the fluid volume of the air pressure adjustment part decreases, and based on the air pressure of the internal part of the middle ear being lower than the air pressure of the external auditory meatus, adjust the air pressure difference by moving the air pressure adjustment device so that the fluid volume of the air pressure adjustment part increases.

The processor may adjust a moving speed of the air pressure adjustment device according to a change speed corresponding to one profile selected from a plurality of profiles associated with a change speed of the fluid volume of the air pressure adjustment part.

The processor may adjust a moving speed of the air pressure adjustment device based on an air pressure adjustment plan inside an airplane according to a flight plan of the airplane.

The processor may, based on an air pressure difference with a sign opposite to an air pressure difference that is a reference of the adjustment being measured while moving the air pressure adjustment device in one direction along the air pressure adjustment part to adjust the air pressure difference, move the air pressure adjustment device in a direction opposite to the one direction.

The main body or the air pressure adjustment device may further include an open tube configured to be openable for opening the external auditory meatus sealed according to wearing of the earplug, and the processor may, while adjusting the air pressure difference by moving the air pressure adjustment device in a direction along the air pressure adjustment part, based on an air pressure difference having a sign opposite to a sign of the air pressure difference that is a reference of the adjustment being measured, open the sealed external auditory meatus by opening the open tube.

The processor may, based on the air pressure difference not being adjusted according to moving of the air pressure adjustment device, output a notification indicating that the external auditory meatus is not sealed.

According to an embodiment, a method for adjusting an air pressure of an air pressure adjustment apparatus including a speaker, a microphone, an earplug of which a main body is made of an elastic material so as to seal an external auditory meatus, based on the earplug being worn on the ear of a user, and which comprises an air pressure adjustment part penetrating the main body includes outputting a sound through the speaker based on the earplug being worn, outputting a sound through the speaker based on the earplug being worn, measuring the air pressure difference between air pressure of an internal part of the middle ear and air pressure of an external auditory meatus on the basis of strength of a received eco based on the echo of the sound reflected from the eardrum of the user being received through the microphone, and adjusting the air pressure difference by moving the air pressure adjustment device according to the measured air pressure difference.

The air pressure adjustment apparatus may further include an air pressure sensor configured to sense the air pressure of the external auditory meatus, and the measuring may include determining air pressure of the internal part of the middle ear on the basis of data relating to the echo strength according to the air pressure of the internal part of the middle ear, and sensing the air pressure of the external auditory meatus through the air pressure sensor.

The adjusting may include calculating a change amount of the fluid volume of the air pressure adjustment part corresponding to the measured air pressure difference, and moving the air pressure adjustment device so that the fluid volume of the air pressure adjustment part changes according to the calculated change amount.

The adjusting may include, based on the air pressure of the internal part of the middle ear being higher than the air pressure of the external auditory meatus, moving the air pressure adjustment device so that the fluid volume of the air pressure adjustment part decreases, and based on the air pressure of the internal part of the middle ear being lower than the air pressure of the external auditory meatus, moving the air pressure adjustment device so that the fluid volume of the air pressure adjustment part increases.

The adjusting may include adjusting a moving speed of the air pressure adjustment device according to a change speed corresponding to one profile selected from a plurality of profiles associated with a change speed of the fluid volume of the air pressure adjustment part.

The adjusting may include adjusting a moving speed of the air pressure adjustment device based on an air pressure adjustment plan inside an airplane according to a flight plan of the airplane.

The adjusting may include, based on an air pressure difference with a sign opposite to an air pressure difference that is a reference of the adjustment being measured while moving the air pressure adjustment device in one direction along the air pressure adjustment part to adjust the air pressure difference, moving the air pressure adjustment device in a direction opposite to the one direction.

The main body or the air pressure adjustment device may further include an open tube configured to be openable for opening the external auditory meatus sealed according to wearing of the earplug, and the adjusting may include, while adjusting the air pressure difference by moving the air pressure adjustment device in a direction along the air pressure adjustment part, based on an air pressure difference having a sign opposite to a sign of the air pressure difference that is a reference of the adjustment being measured, opening the sealed external auditory meatus by opening the open tube.

The method may further include, based on the air pressure difference not being adjusted according to moving of the air pressure adjustment device, outputting a notification indicating that the external auditory meatus is not sealed.

As described above, according to various embodiments, an air pressure difference may be automatically adjusted by measuring an air pressure difference between the internal part of the middle ear and the external auditory meatus. Accordingly, an inconvenience to a user's ear attributable to an air pressure difference may be overcome and a convenience to a user may be improved.

DETAILED DESCRIPTION OF EXAMPLE EMBODIMENTS

Figure 1A:
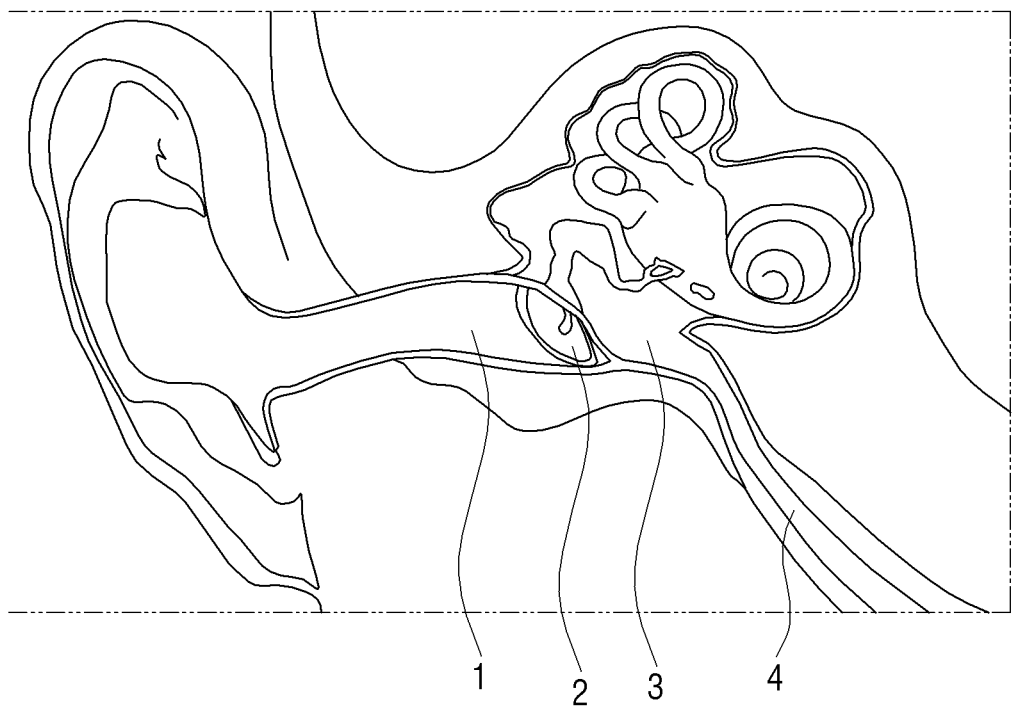
FIG. 1A is a diagram illustrating a structure of an ear of a person.
Figure 1B:
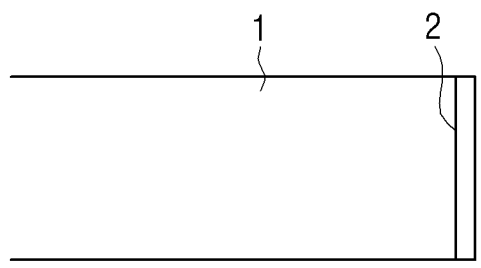
FIG. 1B is a diagram illustrating a state of eardrum according to external air pressure and air pressure of an internal part of a middle ear.
Figure 1B:
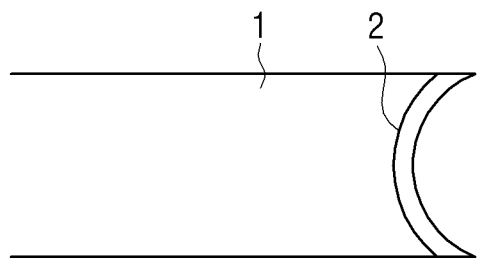
Figure 1B:
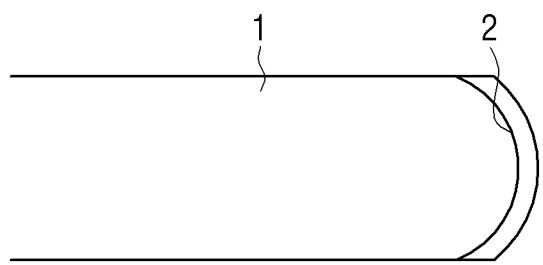

Hereinafter, embodiments of the disclosure will be described with reference to the accompanying drawings. However, it may be understood that the disclosure is not limited to the embodiments described hereinafter, but include various modifications, equivalents, and alternatives of the embodiments of the disclosure. For the description of the drawings, similar reference numerals may be used for similar constituent elements.

In the disclosure, the term "has," "may have," "includes" or "may include" indicates existence of a corresponding feature (e.g., a numerical value, a function, an operation, or a constituent element such as a component), but does not exclude existence of an additional feature.

In the disclosure, the term "A or B," "at least one of A or/and B," or "one or more of A or/and B" may include all possible combinations of the items that are enumerated together. For example, the term "A or B", "at least one of A and B", or "at least one of A or B" may designate (1) at least one A, (2) at least one B, or (3) both at least one A and at least one B.

In the disclosure, the terms "first, second, etc." may be used to describe various elements regardless of their order and/or importance and to discriminate one element from other elements, but are not limited to the corresponding elements.

If it is described that an element (e.g., first element) is "operatively or communicatively coupled with/to" or is "connected to" another element (e.g., second element), it may be understood that the element may be connected to the other element directly or through still another element (e.g., third element). When it is mentioned that one element (e.g., first element) is "directly coupled" with or "directly connected to" another element (e.g., second element), it may be understood that there is no element (e.g., third element) present between the element and the other element.

Herein, the expression "configured to" may be used interchangeably with, for example, "suitable for", "having the capacity to", "designed to", "adapted to", "made to", or "capable of". The expression "configured to" does not necessarily mean "specifically designed to" in a hardware sense. Instead, under some circumstances, "a device configured to" may indicate that such a device may perform an operation along with another device or part. For example, the expression "a processor configured to perform A, B, and C" may indicate an exclusive processor (e.g., an embedded processor) to perform the corresponding operation, or a generic-purpose processor (e.g., a central processor (CPU) or application processor (AP)) that may perform the corresponding operations by executing one or more software programs stored in the memory device.

Hereinbelow, various embodiments will be described in greater detail with reference to accompanying drawings.

Figure 2A:
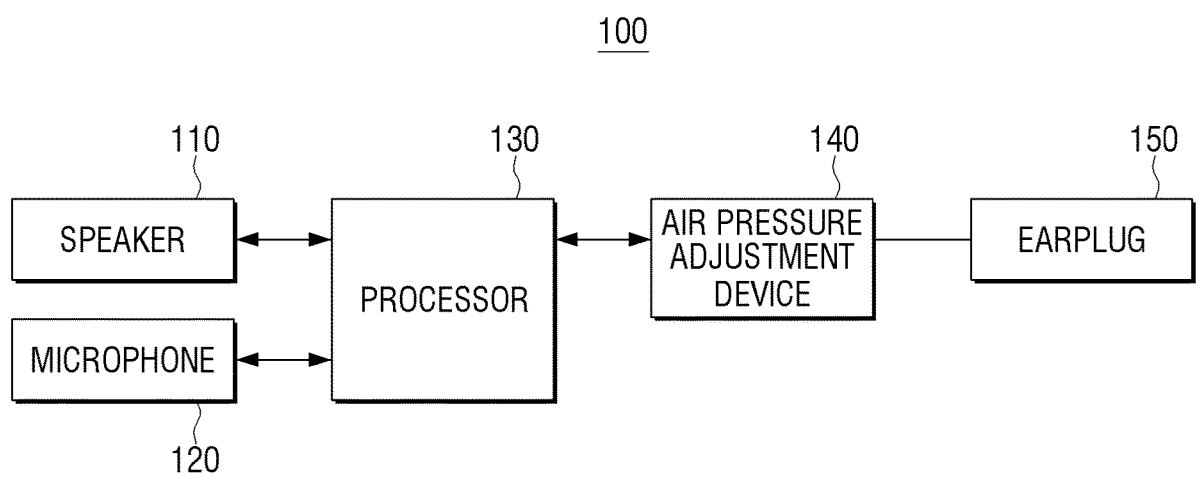
FIG. 2A is a block diagram of an air pressure adjustment apparatus according to an embodiment.

FIG. 2A is a block diagram of an air pressure adjustment apparatus according to an embodiment. According to FIG. 2A, an air pressure adjustment apparatus 100 includes a speaker 110, a microphone 120, a processor 130, an air pressure adjustment device 140, and an earplug 150.

The speaker 110 generates a sound. The speaker 110 may be controlled by the processor 130 to generate a sound. The sound refers to a not having one or more frequencies. The microphone 120 may receive external soundwave or ultrasonic wave from the outside, generate the electrical signal according to the vibration thereof, and transmit the generated electrical signal to the processor 130.

The earplug 150 may include a main body 151 made of an elastic material and an air pressure adjustment part 153 penetrating the main body 151. The main body 151 is made of an elastic material and the earplug 150, when worn on the ear of a user, may seal the external auditory meatus 1 of the user from the outside. The air pressure adjustment device 140 may adjust the fluid volume inside the air pressure adjustment part 153. For example, the air pressure adjustment device 140 may move along the air pressure adjustment part 153 to adjust the internal fluid volume of the air pressure adjustment part 153. If the air pressure adjustment device 140 is connected to the air pressure adjustment part 153 through a pipe and thus is present in the outside, the air pressure adjustment device 140 may move along the pipe to adjust the fluid volume inside the air pressure adjustment part 153.

Figure 2B:
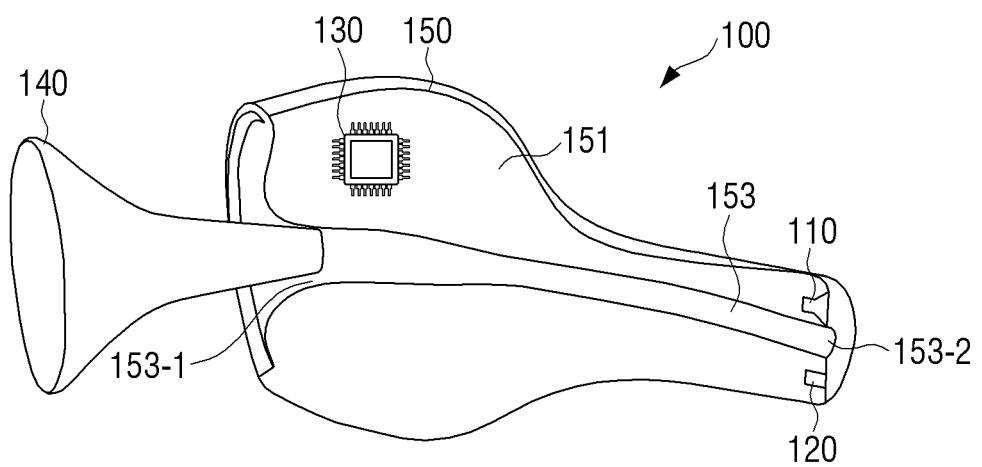
FIG. 2B is a cross-sectional diagram of an air pressure adjustment apparatus according to an embodiment.
Figure 2C:
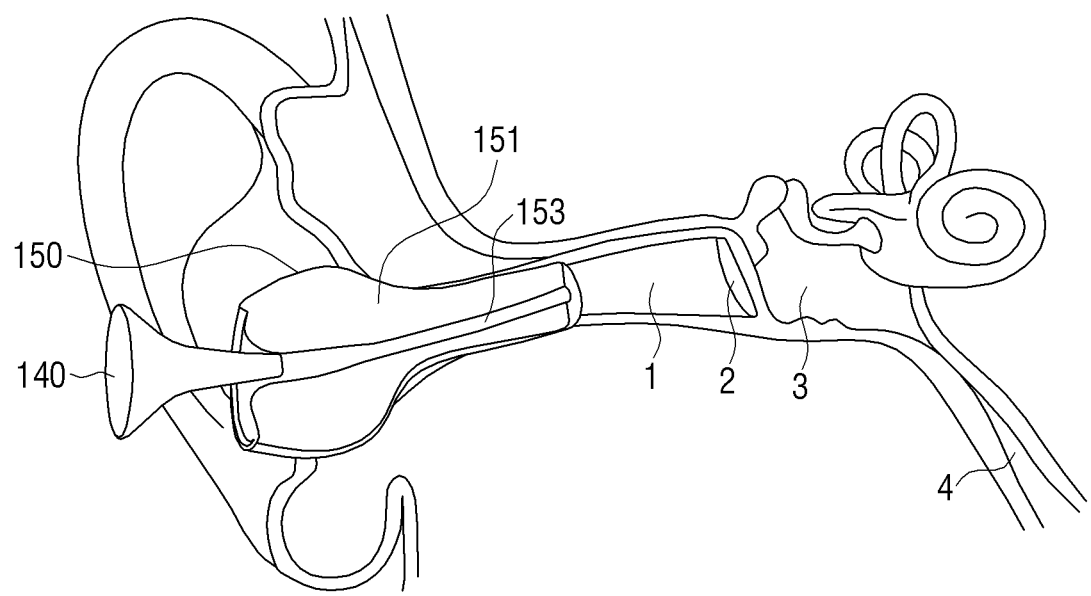
FIG. 2C illustrates an example of wearing an air pressure adjustment apparatus according to an embodiment.

FIG. 2B is a cross-sectional diagram of the air pressure adjustment apparatus 100 according to an embodiment, and FIG. 2C illustrates an example of wearing the air pressure adjustment apparatus 100 according to an embodiment. As described above, the main body 151 of the earplug 150 is made of an elastic material and thus, when the earplug 150 is worn on the ear of a user, as illustrated in FIG. 2C, the earplug 150 may seal the external auditory meatus 1 of a user from the outside.

As illustrated in FIG. 2B, the earplug 150 may include an air pressure adjustment part 153 penetrating the main body 151, and the air pressure adjustment device 140 may be located at one end 153-1 of the air pressure adjustment part 153 and move along the air pressure adjustment part 153. The air pressure adjustment device 140 may be directly connected to the air pressure adjustment part 153 or may be connected by a pipe and present in the outside. The air pressure adjustment device 140 may be attached to the air pressure adjustment part 153 or the pipe for moving, and may change the internal fluid volume of the air pressure adjustment part 153 as much as the moving.

The elastic material forming the main body 151 may include, for example, rubber or sponge, but is not limited thereto. The air pressure adjustment part 153 or the air pressure adjustment device 140 may be manufactured in various ways through various materials that are suitable for performing a function or an operation described in the disclosure. For example, it is desirable that the fluid volume inside the air pressure adjustment part 153 is not changed according to the deformation of the main body 151 due to wearing of the earplug by the user and thus, the air pressure adjustment part 153 may be made of a material different from the main body 151 to have a relatively stronger strength compared to the main body 151, but is not limited thereto. A material or a manufacturing method of the air pressure adjustment part 153 and the air pressure adjustment device 140 is not related to the gist of the disclosure and thus a detailed description will be omitted.

The processor 130 controls overall operation of the air pressure adjustment apparatus 100. The processor 130 may control the speaker 110 to output sound when the earplug 150 is worn. According to an embodiment, the sound may be a pure tone but is not limited thereto.

When the echo reflected from the eardrum 2 of the user is received through the microphone 120, the processor 130 may measure the air pressure difference between the air pressure of the internal part of the middle ear 3 and the air pressure of the external auditory meatus 1 based on the received strength (or energy) of the echo.

For example, when the processor 130 receives the echo, the processor 130 may determine the air pressure difference between the air pressure of the internal part of the middle ear 3 and the air pressure of the external auditory meatus 1 of the user using the echo strength (or energy) according to the air difference between the internal part of the middle ear 3 and air pressure of the external auditory meatus 1. When receiving the echo, the processor 130 may determine the air pressure of the internal part of the middle ear 3 of the user using the echo strength (or energy) data according to the air pressure of the internal part of the middle ear 3, measure the air pressure of the external auditory meatus 1, to calculate the air pressure difference between the air pressure of the internal part of the middle ear 3 and the air pressure of external auditory meatus 1.

Figure 3A:
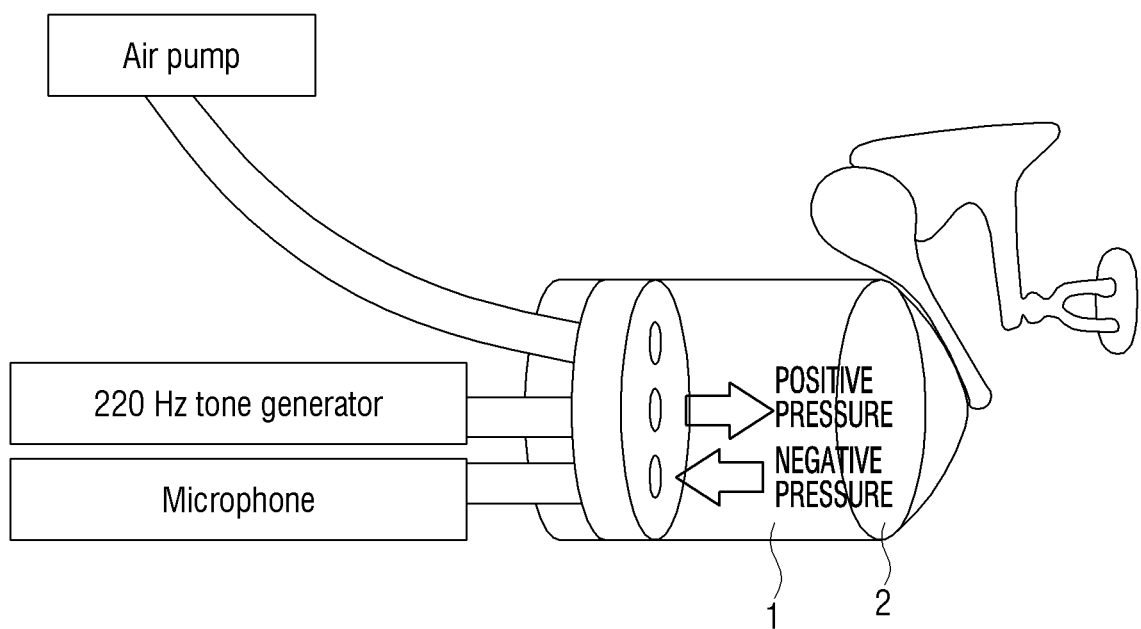
FIG. 3A is a diagram illustrating tympanometry.
Figure 3B:
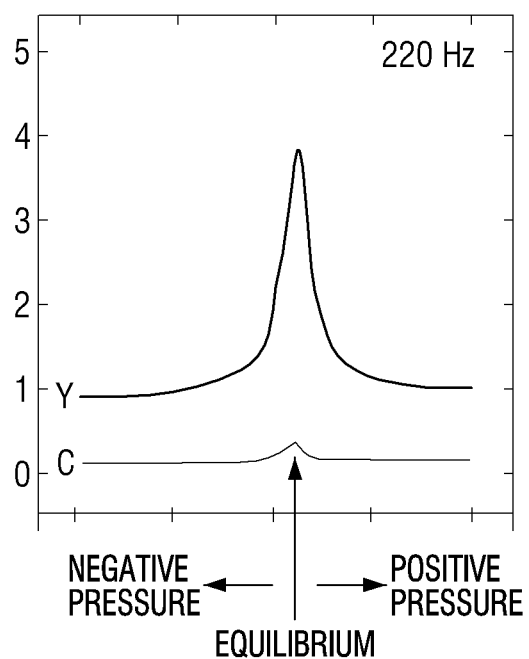
FIG. 3B is an exemplary diagram of a result of the tympanometry for a normal eardrum.

Referring to FIGS. 3A and 3B, the operation of measuring the air pressure difference between the air pressure of the internal part of the middle ear 3 and the air pressure of the external auditory meatus 1 of a user will be described in greater detail. FIG. 3A is a diagram illustrating tympanometry and FIG. 3B illustrates a result of tympanometry for a normal eardrum.

The tympanometry is a test for measuring a state of the eardrum 2 through echo reflected from the eardrum 2 by generating a pure sound while adjusting the air pressure in the external auditory meatus through an air pump. FIG. 3A illustrates that the strength (or energy) of echo of the pure sound of 220 Hz is measured while applying pressure to the external auditory meatus 1 via an air pump.

FIG. 3B illustrates the strength (or energy) of echo according to the pressure applied to the external auditory meatus 1 via an air pump. Referring to FIG. 3B, when the eardrum 2 is in equilibrium, the strength (or energy) of the echo is measured to be highest, and that the strength (or energy) of the echo is lowered when the eardrum 2 is expanded in the middle ear or external auditory meatus direction by applying a positive pressure (pressure in the eardrum direction) or a negative pressure (pressure in the opposite direction of the eardrum) to the external auditory meatus 1 through the air pump. That is, according to the air pressure difference of the internal part of the middle ear and the air pressure of the external auditory meatus, deformation of the eardrum occurs, and this may cause the strength (or energy) of the echo of the same frequency to be vary with respect to the pure sound of a specific frequency.

Various embodiments may, conversely, estimate the air pressure difference between the air pressure of the internal part of the middle ear and the air pressure of the external auditory meatus by determining the air pressure of the internal part of the middle ear or the air pressure difference corresponding to the measured strength (or energy) of the echo, on the data relating to the strength (or energy) of the echo according to the pre-obtained air pressure difference between the air pressure of the internal part of the middle ear and the air pressure of the external auditory meatus of a person or data relating to the strength (or energy) of the echo according to the internal part of the middle ear of a person.

According to an embodiment, when the echo is received, the processor 130 may measure the strength (or energy) of the echo, and measure or determine the air pressure difference corresponding to the measured strength (or energy) of the echo on the data of the echo strength (or energy) according to the air pressure difference between the internal part of the middle ear and the external auditory meatus as the air pressure difference between the air pressure of the internal part of the middle ear 3 and the air pressure of the external auditory meatus 1.

According to another embodiment, the processor 130 may measure the strength (or energy) of the echo when the echo is received, determine the air pressure of the internal part of the middle ear corresponding to the measured strength (or energy) of the echo on the data of echo strength (or energy) according to the air pressure of the internal part of the middle ear, and detect the air pressure of external auditory meatus 1 via a separate air pressure sensor (not shown) to measure the air pressure difference between the air pressure of the internal part of the middle ear 3 and the air pressure of external auditory meatus 1.

As described above, if the air pressure difference between the air pressure of internal part of middle ear 3 and the air pressure of external auditory meatus 1 is measured, the processor 130 may move the air pressure adjustment device 140 according to the measured air pressure difference to adjust the air pressure difference.

The processor 130 may calculate the fluid volume change amount inside the air pressure adjustment part 153 corresponding to the air pressure difference and move the air pressure adjustment device 140 so that the fluid volume inside the air pressure adjustment part 153 changes as much as the calculated change amount.

Referring to FIG. 2B, the air pressure adjustment device 140 is located at one end 153-1 of the air pressure adjustment part 153 and closely move along the air pressure adjustment part 153 and thus, the fluid volume of the air pressure adjustment part 153 may be changed by moving the air pressure adjustment device 140.

As illustrated in FIG. 2C, when the earplug 150 is worn on the user's ear, the external auditory meatus 1 is sealed and the other end 153-2 of the air pressure adjustment part 153 is open in the external auditory meatus 1 direction, so that the fluid volume inside the air pressure adjustment part 153 is changed by the changed fluid volume when the processor 130 moves the air pressure adjustment device 140 to change the fluid volume inside the air pressure adjustment part 153.

The processor 130 may change the fluid volume inside the external auditory meatus 1 by moving the air pressure adjustment device 140, to adjust the air pressure difference between the air pressure of the internal part of the middle ear 3 and the air pressure of the internal part of the external auditory meatus 1.

According to an embodiment, when the air pressure of the internal part of the middle ear 3 is higher than the air pressure of the external auditory meatus 1, the processor 130 may move the air pressure adjustment device 140 to reduce the fluid volume of the air pressure adjustment part 153, and when the air pressure of the internal part of the middle ear 3 is lower than the air pressure of external auditory meatus 1, the processor 130 may move the air pressure adjustment device 140 to increase the fluid volume of the air pressure adjustment part 153 to adjust the air pressure difference.

The processor 130 may adjust the air pressure difference by increasing the air pressure of the external auditory meatus 1 when the air pressure of the internal part of the middle ear 3 is higher than the air pressure of external auditory meatus 1, and by decreasing the air pressure of the external auditory meatus 1 when the air pressure of the internal part of the middle ear 3 is lower than the air pressure of external auditory meatus 1, so that the air pressure difference with the air pressure of the internal part of the middle ear 3 is decreased.

Figure 4:
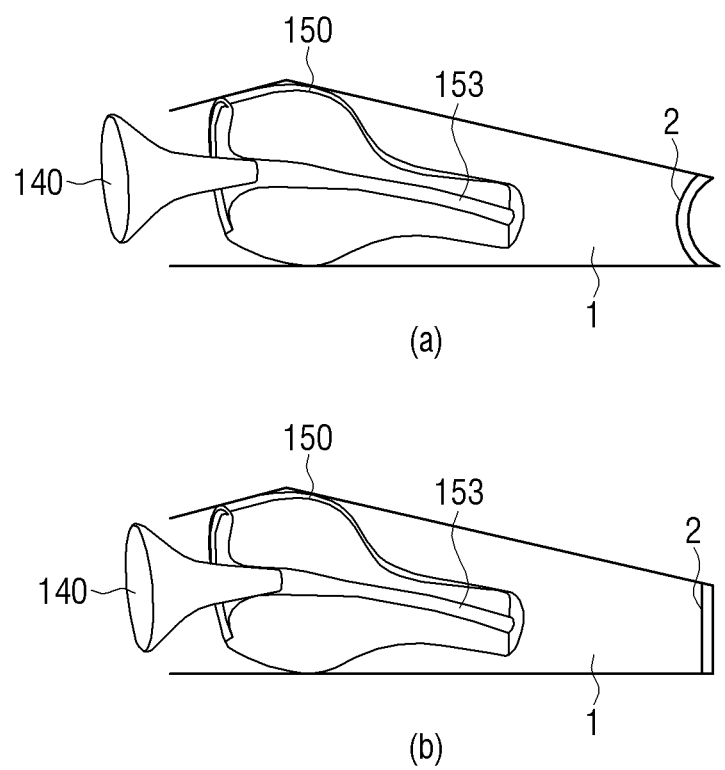
FIG. 4 is an exemplary diagram illustrating an operation of an air pressure adjustment apparatus when air pressure of the internal part of the middle ear is higher than the air pressure of the external auditory meatus.

FIG. 4 is an exemplary diagram illustrating an operation of the air pressure adjustment apparatus 100 when air pressure of the internal part of the middle ear 3 is higher than the air pressure of the external auditory meatus 1. Both FIGS. 4A and 4B illustrate that the earplug 150 is worn on the ear of the user and the external auditory meatus 1 is sealed.

When the air pressure of the internal part of the middle ear 3 of the user is higher than the air pressure of external auditory meatus 1, it can be seen that the eardrum 2 is expanded in the external auditory meatus 1 direction, as shown in FIG. 4A. When the earplug 150 is worn, the processor 130 may output a sound to receive the echo reflected from the eardrum 2, and based on the strength (or energy) of the echo, may measure the air pressure difference between the internal part of the middle ear 3 and the external auditory meatus 1. In FIG. 4A, since the air pressure of the internal part of the middle ear 3 is measured higher than the external auditory meatus 1 air pressure, the processor 130 moves the air pressure adjustment device 140 to reduce the fluid volume inside the air pressure adjustment part 153.

Accordingly, since the gas molecules contained in the fluid volume inside the reduced air pressure adjustment part 153 are moved along the air pressure adjustment part 153 to a space of the sealed external auditory meatus 1, the external auditory meatus 1 increases the number of gas molecules per unit volume, thereby increasing the air pressure. It is apparent that the greater the air pressure adjustment device 140 moves in the direction of the eardrum 2, the more gas molecules are moved into the space of the sealed external auditory meatus 1, and the air pressure of the external auditory meatus 1 will rise further. As such, when the air pressure of the internal part of the middle ear 3 is higher than the air pressure of the external auditory meatus 1, the processor 140 may adjust the air pressure difference by increasing the air pressure of the external auditory meatus 1.

According to one embodiment, the processor 130 may calculate a fluid volume change amount of the air pressure adjustment part 153 corresponding to the air pressure difference between the air pressure of the internal part of the middle ear 3 and the air pressure of the external auditory meatus 1, wherein the fluid volume change amount may be a fluid volume change amount such that the air pressure of the internal part of the middle ear 3 and the air pressure of the external auditory meatus 1 are in equilibrium.

The processor 130 may move the air pressure adjustment device 140 to adjust the air pressure difference so that the air pressure of the internal part of the middle ear 3 and the air pressure of the external auditory meatus 1 are in equilibrium, as shown in FIG. 4B. FIG. 4B illustrates that the air pressure of the internal part of the middle ear 3 and the air pressure of the external auditory meatus 1 are equilibrated to the state in which the eardrum 2 is in equilibrium.

If the air pressure of the internal part of the middle ear 3 is lower than the air pressure of the external auditory meatus 1, on the contrary to FIG. 4A, it will be readily understood by those skilled in the art that the eardrum 2 is expanded in the direction opposite to the external auditory meatus 1, that is, in the direction of the internal part of the middle ear 3, and accordingly, the processor 130 may move the air pressure adjustment device 140 to increase the fluid volume inside the air pressure adjustment part 153 so that the air pressure of the internal part of the middle ear 3 and the air pressure of the external auditory meatus 1 are in equilibrium.

According to an embodiment, the processor 130 may measure the air pressure difference by repeating with a predetermined cycle, and accordingly, the processor 130 may track and adjust the air pressure difference which continuously occurs. When measuring the air pressure difference repeatedly, the processor 130 may adjust the speaker 110 to generate a sound having a frequency beyond an audible frequency range, but the embodiment is not limited thereto.

The processor 130 may include one or more of a central processing unit (CPU), a controller, an application processor (AP), a communication processor (CP) an advanced reduced instruction set computer (RISC) machines (ARM) processor, Micom, or the like.

FIG. 2B illustrates an in-ear type air pressure adjustment apparatus 100 in which the speaker 110, the microphone 120, and the processor 130 are all implemented to be included in the body 151 of the earplug 150. However, the embodiment is not limited thereto, and a neck band type or an earphone type air pressure adjustment apparatus 100 which places the processor 130 or the air pressure adjustment device 140 outside the earplug 150 is also available.

FIG. 2B illustrates an example in which the speaker 110 and the microphone 120 for measuring the air pressure difference are disposed at the end of the main body 151 that is opposite to the air pressure adjustment device 140 with reference to the air pressure adjustment part 153. According to an embodiment, the speaker 110 and the microphone 120 may be disposed on different parts of the main body 151.

Figure 5:
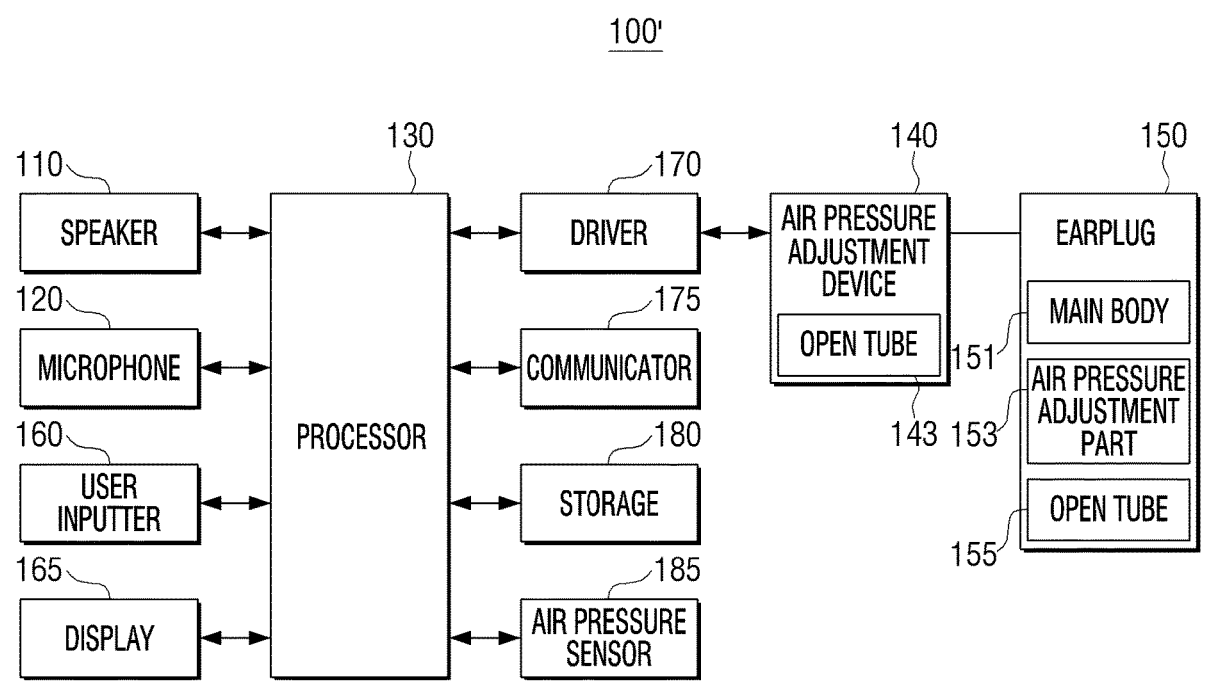
FIG. 5 is a detailed block diagram of an air pressure adjustment apparatus according to an embodiment.

FIG. 5 is a detailed block diagram of an air pressure adjustment apparatus according to an embodiment. Referring to FIG. 5, an air pressure adjustment apparatus 100' may include the speaker 110, the microphone 120, the processor 130, the air pressure adjustment device 140, the earplug 150, a user inputter 160, a display 165, a driver 170, a communicator 175, a storage 180, and an air pressure sensor 185. It is not mandatory that all the configurations of the air pressure adjustment apparatus 100' shown in FIG. 5 should be included in the air pressure adjustment apparatus 100', and in accordance with an embodiment, some configurations may be omitted, and other configurations may be added. In describing FIG. 5, descriptions of the air pressure adjustment apparatus 100 described above will be omitted.

The user inputter 160 is configured to receive a user command for controlling the air pressure adjustment apparatus 100'. The user inputter 160 may receive a user command to select any one of a plurality of profiles relating to the rate of change of the fluid volume of the air pressure adjustment part 153, which will be further described below. For this purpose, the user inputter 160 may be implemented with various buttons or touch panels, but is not limited thereto.

The display 165 displays various images and texts. For example, the display 165 may display a plurality of profiles relating to the rate of change of the fluid volume of the air pressure adjustment part 153. The display 165 may output a message informing that the external auditory meatus 1 is not sealed even if the user wears the earplug 150 on the ear as described below. The display 165 may include, but is not limited to, a liquid crystal display (LCD) or a light emitting diode (LED).

The driver 170 controls the air pressure adjustment device 140 under the control of the processor 130. As described above, the processor 130 moves the air pressure adjustment device 140 to adjust the air pressure difference, where the air pressure adjustment device 140 may be moved through the driver 170 implemented with a motor, a pump, or the like. That is, the processor 130 may control the driver 170 to move the air pressure adjustment device 140.

The communicator 175 may communicate with an external device to transmit and receive various information. The communicator 175 may receive information regarding external air pressure from an external server or a terminal device, information on an internal air pressure control plan of the airplane according to the flight plan of the airplane. The communicator 175 may include at least one of a wireless communication chip (not shown) and a local area communication chip (not shown).

The storage 180 stores various programs and data. The storage 180 may store a plurality of profile information relating to the rate of change of the fluid volume of the air pressure adjustment part 153, information on the air pressure adjustment plan of the airplane according to the flight plan of the airplane, echo strength (or energy) data according to the air pressure difference of the internal air pressure and the air pressure of the external auditory meatus, information on the amount of movement of the air pressure adjustment device 140 corresponding to the fluid volume change amount of the air pressure adjustment part 153, or the like.

For this purpose, the storage 180 may include, but is not limited to, a random access memory (RAM), a read only memory (ROM), a solid state memory disk (SSD), various semiconductor memories such as flash memory, a hard disk, and an optical storage medium such as a magnetic storage medium or a compact disc (CD). According to an embodiment, the storage 180 may be implemented with a cloud server that provides various information or data through the communicator 175.

The air pressure sensor 185 may measure external air pressure of the air pressure adjustment apparatus 100' or air pressure of the external auditory meatus 1.

At least one of the air pressure adjustment device 140 and the earplug 150 may include an open tube 143, 155. The open tube 143, 155 may be opened and closed, and is configured to connect the sealed external auditory meatus 1 according to wearing of the earplug 150 with the outside of the air pressure adjustment apparatus 100' for opening. A detail thereof will be described below.

Although not illustrated in the drawings, the air pressure adjustment apparatus 100' may separately include a wearing detection sensor that senses whether the earplug 150 is worn on the user's ear. The wearing detection sensor may be implemented with various sensors, such as, but not limited to, a temperature sensor, an infrared sensor, a touch sensor, a gyro sensor, or the like.

The processor 130 controls the overall operation of the air pressure adjustment apparatus 100'. The processor 130 may adjust the rate of movement of the air pressure adjustment device 140 according to a rate of change corresponding to a selected one of a plurality of profiles relating to the rate of change of the fluid volume of the air pressure adjustment part 153.

As described above, the processor 130 may calculate a fluid volume change amount of the air pressure adjustment part 153 corresponding to the air pressure difference between the internal part of the middle ear 3 and the external auditory meatus 1, and move the air pressure adjustment device 140 to change the fluid volume of the air pressure adjustment part 153 by the calculated change amount, so that the processor 130 may adjust the air pressure adjustment speed, that is, the moving speed of the air pressure adjustment device 140, based on various information. Even if the air pressure difference between the internal part of the middle ear 3 and the external auditory meatus 1 occurs, the rate of adjustment of the air pressure difference desired by the user may vary by users.

According to one embodiment, a user may select one of a plurality of profiles relating to the rate of fluid volume change of the air pressure adjustment part 153 through the user interface 160. Accordingly, the processor 130 may adjust the moving speed of the air pressure adjustment device 140 according to the rate of change corresponding to the selected profile.

An airplane is provided with an airplane internal pressure adjustment plan in accordance with the flight plan, to make a user adapt to changes in the altitude of the airplane. Even if the internal air pressure of the airplane is adjusted according to the internal air pressure adjustment plan, the difference of the air pressure between the air pressure of the internal part of the middle ear 3 and the air pressure of the external auditory meatus 1 occurs. According to one embodiment, the processor 130 may adjust the moving speed of the air pressure adjustment device 140 in accordance with an airplane internal pressure control plan to provide an optimal air pressure adjustment experience for a user riding in the airplane. Here, information about the air pressure adjustment plan of the airplane may be obtained from an airline server or a computer system of the airplane via the communicator 175.

While the air pressure adjustment device 140 is moved and the air pressure difference is adjusted based on the measured air pressure difference, if the air pressure difference having an opposite sign as the air pressure difference that is the basis of the current adjustment is measured, the processor 130 may stop adjustment of the former air pressure difference.

Figure 6:
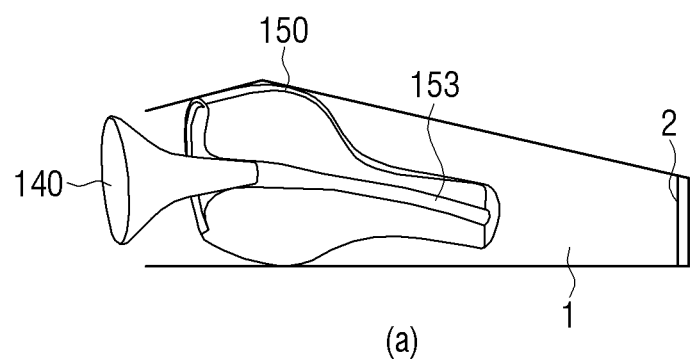
FIG. 6 is an exemplary view illustrating an operation of an air pressure adjustment apparatus when an air pressure difference having an opposite signal is measured during adjustment of the air pressure difference.
Figure 6:
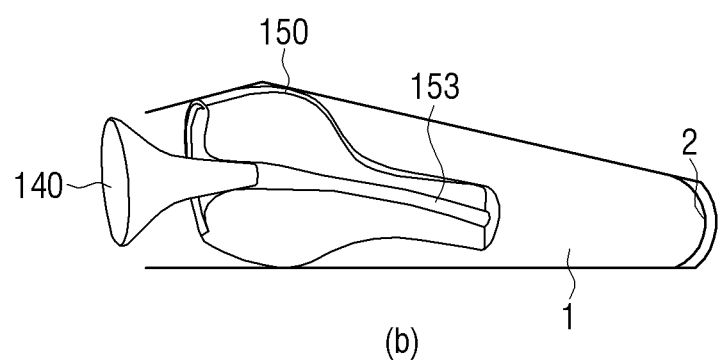
Figure 6:
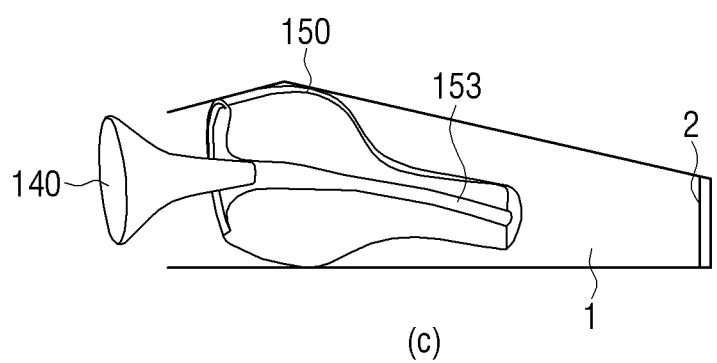

Referring to FIG. 6, more detailed description will be provided below. FIG. 6 is an exemplary diagram illustrating an operation of the air pressure adjustment apparatus 100' in a case where the air pressure difference of an opposite sign is measured during the air pressure difference adjustment.

FIG. 6A illustrates a situation as shown in FIG. 4B. In other words, as shown in FIG. 4A, the air pressure of the internal part of the middle ear 3 is measured to be higher than the air pressure of the external auditory meatus 1, so that the processor 130 moves the air pressure adjustment device 140 in the direction of the eardrum 2 so as to the air pressure of the internal part of the middle ear 3 and the air pressure of the external auditory meatus 1 are in equilibrium.

As described above, when the user's Eustachian tube 4 is opened while the air pressure difference is adjusted, the air pressure of the internal part of the middle ear 3 and the external air pressure become equal, a pressure difference of which sign is opposite to the air pressure difference which is a basis for the air pressure adjustment operation for the external auditory meatus 1 may occur. That is, the air pressure of the internal part of the middle ear 3 is lower than the air pressure of the external auditory meatus 1, and as shown in FIG. 6B, the eardrum 2 expands in the direction of the internal part of the middle ear 3. This pressure difference can also cause pain to the ear or a feeling as if the ear is popping to a user.

According to one embodiment, while the air pressure adjustment device 140 is moved in one direction along the air pressure adjustment part 153 and the air pressure difference is adjusted, if the air pressure difference having an opposite sign as the air pressure difference that is the basis of the current adjustment is measured, the processor 130 may move the air pressure adjustment device 140 in a direction opposite to the one direction above.

Since the processor 130 may continuously measure the pressure difference at a predetermined period, as shown in FIG. 6B, when a pressure difference of the opposite sign is generated as shown in FIG. 6B, the processor 130 may immediately detect the pressure difference. Accordingly, the processor 130 may move the air pressure adjustment device 140 in the opposite direction of the eardrum 2, as shown in FIG. 6C, so that the air pressure of the internal part of the middle ear 3 and the air pressure of the external auditory meatus 1 is adjusted to be in equilibrium.

Figure 7:
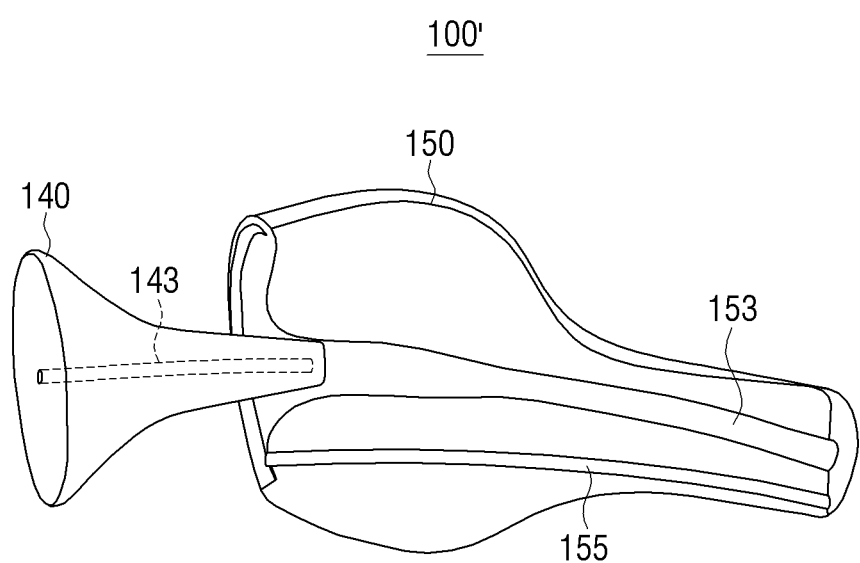
FIG. 7 is another exemplary diagram illustrating an operation of an air pressure adjustment apparatus when the air pressure difference having an opposite sign is measured during adjusting the air pressure difference.

An example in which the pressure difference having the opposite sign is measured during the air pressure adjustment is measured so that the existing air pressure difference adjustment is stopped is not limited to the above example. According to another embodiment, the main body 151 of the earplug 150 or the air pressure adjustment device 140 may further include the open tube 143, 155 which may be opened and closed, for opening the sealed external auditory meatus 1 according to the wearing of the earplug 150, as described above. FIG. 7 illustrates an example of the main body 151 of the earplug 150 and the open tubes 143, 155 included in the air pressure adjustment device 140.

Accordingly, when the air pressure adjustment device 140 is moved in one direction along the air pressure adjustment part 153 to adjust the pressure difference, if the pressure difference of which sign is opposite to the air pressure difference that is the basis for the adjustment is measured, the processor 130 may immediately open the open tubes 143 and 155 to open the sealed external auditory meatus 1. As illustrated in FIG. 6B, when the air pressure difference having an opposite signal is generated, the air pressure of the internal part of the middle ear 3 is equal to the external air pressure, and when the open tube 143, 155 is opened as above, the air pressure of the external auditory meatus 1 is also equal to the external air pressure, so that the air pressure of the internal part of the middle ear 3 and the air pressure of the external auditory meatus 1 may be in equilibrium.

According to an embodiment, the processor 130 may identify (or determine) a state of wearing the earplug 150 of the user. The processor 130 may identify whether the earplug 150 is worn correctly to seal the external auditory meatus 1.

Specifically, when the earplug 150 is worn, the processor 130 first moves the air pressure adjustment device 140 and then measures the pressure difference to determine whether the air pressure difference is adjusted according to the movement of the air pressure adjustment device. If the earplug 150 is worn correctly, the external auditory meatus 1 is sealed, and thus, the air pressure difference is changed according to the movement of the air pressure adjustment device 140, and this may mean that the air pressure difference adjustment is available, but if the earplug 150 is not correctly worn and the external auditory meatus 1 is not sealed, even if the air pressure adjustment device 140 is moved, the air pressure difference would not be changed.

Accordingly, if it is determined that the pressure difference is not adjusted, the processor 130 may output a notification indicating that the external auditory meatus 1 has not been sealed. In this example, the notification may be, for example, but not limited to, a warning sound through the speaker 110 or a voice instruction to guide that the earplug 150 needs to be worn again.

Figure 8:
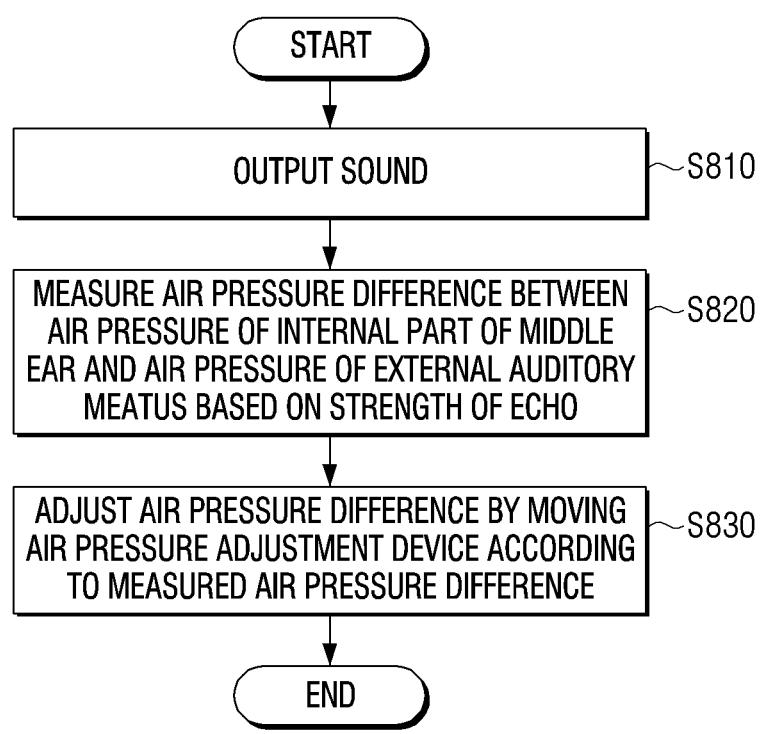
FIG. 8 is a flowchart illustrating a method for adjusting an air pressure of an air pressure adjustment apparatus according to an embodiment.

FIG. 8 is a flowchart illustrating an air pressure adjustment method of an air pressure adjustment apparatus 100, 100' according to an embodiment. The air pressure adjustment apparatus 100, 100' may include the speaker 110, the microphone 120, the earplug 150 of which the main body the main body 151 is made of an elastic material so as to seal the external auditory meatus 1 when the earplug 150 is worn on the ear of a user, and which includes an atmospheric pressure adjustment part 153 penetrating the main body 151, and the air pressure adjustment device 140 for adjusting the fluid volume of the air pressure adjustment part 153 by moving along the air pressure adjustment part 153. In describing FIG. 8, a description overlapping with the above description will be omitted.

Referring to FIG. 8, the air pressure adjustment apparatus 100, 100' may output a sound through the speaker 110 when the earplug 150 is won in operation S810.

Accordingly, when the echo reflected from the eardrum 2 of the user is received through the microphone 120, the air pressure adjustment apparatus 100, 100' can measure the air pressure difference between the air pressure of the internal part of the middle ear 3 and the air pressure of the external auditory meatus 1 based on the strength of the received echo in operation S820.

According to an embodiment, the air pressure adjustment apparatus 100, 100' may further include the air pressure sensor 185 for sensing the air pressure of the external auditory meatus, determine the air pressure of the internal part of the middle ear 3 based on data relating to the echo strength according to the air pressure of the internal part of the middle ear, and calculate a pressure difference between the air pressure of the internal part of the middle ear 3 and the air pressure of the external auditory meatus 1 by sensing the air pressure of the external auditory meatus 1 through the air pressure sensor 185.

According to one embodiment, the air pressure adjustment apparatus 100, 100' may measure the strength (or energy) of the echo when echo is received, and measure the pressure difference corresponding to the measured echo strength (or energy) on the echo strength (or energy) data according to the air pressure difference of the air pressure of the internal part of the middle ear and the air pressure of the external auditory meatus as the air difference between the air pressure of the internal part of the middle ear 3 and the air pressure of the external auditory meatus 1.

When the air pressure difference is measured, the air pressure adjustment apparatus 100, 100' may move the air pressure adjustment device 140 according to the measured air pressure difference to adjust the air pressure difference in operation S830.

For example, the air pressure adjustment apparatus 100, 100' may calculate the change amount of the fluid volume of the air pressure adjustment part 153 corresponding to the measured air pressure difference and may move the air pressure adjustment device 140 so that the fluid volume of the air pressure adjustment part 153 changes by the calculated change amount.

If the air pressure of the internal part of the middle ear 3 is higher than the air pressure of the external auditory meatus 1, the air pressure adjustment apparatus 100, 100' may move the air pressure adjustment device 140 so that the fluid volume of the air pressure adjustment part 153 decreases, and when the air pressure of the internal part of the middle ear 3 is lower than the air pressure of the external auditory meatus 1, may move the air pressure adjustment device 140 so that the fluid volume of the air pressure adjustment part 153 increases.

The air pressure adjustment apparatus 100, 100' may adjust the moving speed of the air pressure adjustment device 140 according to the change speed corresponding to one profile selected among the plurality of profiles relating to the change speed of the fluid volume of the air pressure adjustment part 153. The air pressure adjustment apparatus 100, 100' may adjust the moving speed of the air pressure adjustment device 140 based on the internal air pressure adjustment plan according to the flight plan of an airplane.

If the air pressure difference is not adjusted according to the moving of the air pressure adjustment device 140, the air pressure adjustment apparatus 100, 100' may output a notification that the external auditory meatus 1 is not sealed.

Figure 9:
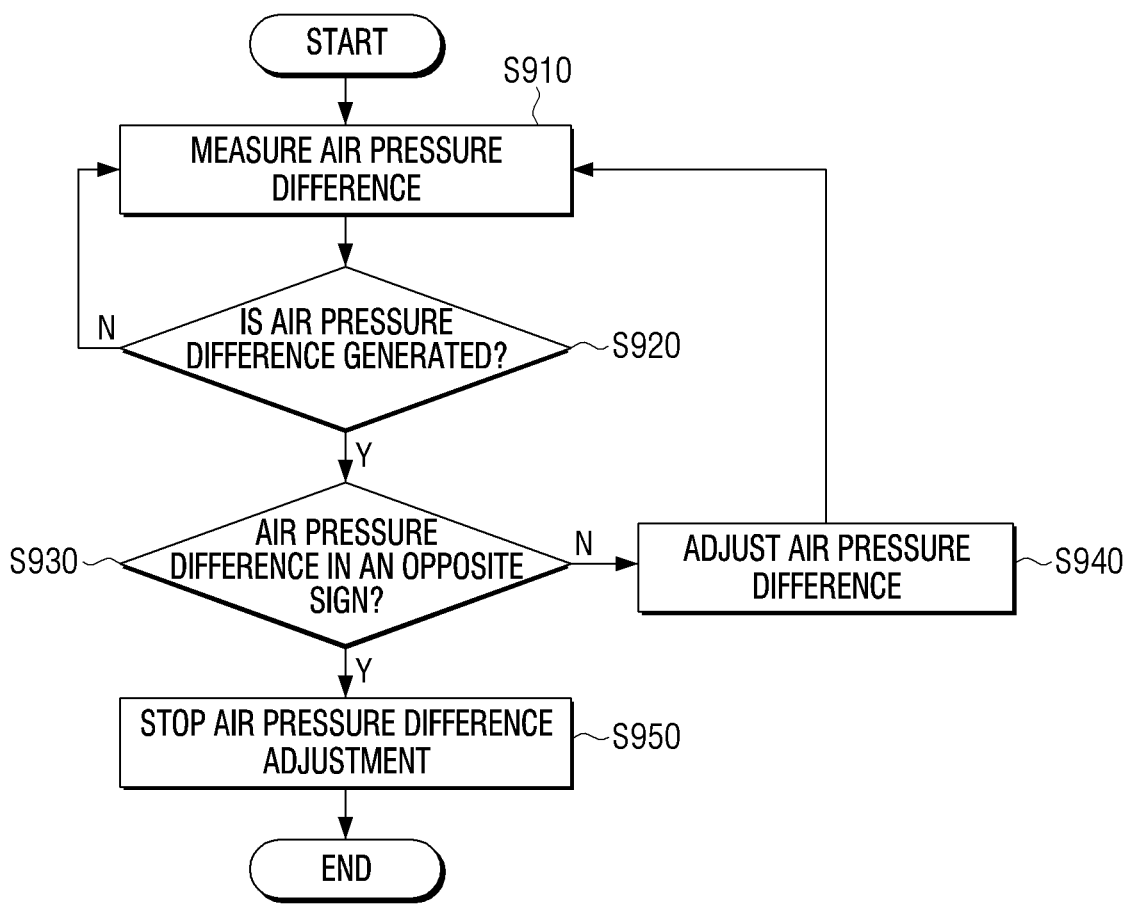
FIG. 9 is a flowchart illustrating a method for adjusting an air pressure of an air pressure adjustment apparatus according to another embodiment.

FIG. 9 is a flowchart illustrating a method for air pressure adjustment of the air pressure adjustment apparatus 100, 100' according to another embodiment. In describing FIG. 9, a description overlapping with the aforementioned description will be omitted. Referring to FIG. 9, the air pressure adjustment apparatus 100, 100' may measure the air pressure difference between the air pressure of the internal part of the middle ear 3 and the air pressure of the external auditory meatus 1 in operation S910. The air pressure adjustment apparatus 100, 100' may determine whether the air pressure difference is generated in operation S920. As a result of determination, if the air pressure difference is not generated in operation S920-N, the air pressure adjustment apparatus 100, 100' may measure the air pressure difference again.

If the air pressure difference is generated in operation S920-Y, the air pressure adjustment apparatus 100, 100' may determine whether the air pressure difference having an opposite sign is generated in operation S930. As a result of the determination, if the air pressure difference having an opposite sign is not generated in operation S930-N, the air pressure adjustment apparatus 100, 100' may adjust the air pressure difference in operation S940 as described above and measure the air pressure difference again.

If the air pressure difference having the opposite sign is generated in operation S930-Y, the air pressure adjustment apparatus 100, 100' may stop adjusting the existing air pressure difference in operation S950. In this example, the air pressure adjustment apparatus 100, 100' may stop the air pressure difference adjustment by moving the air pressure adjustment device 140 in a direction opposite to the former moving direction. The air pressure adjustment apparatus 100, 100' may stop adjusting the air pressure adjustment by making the sealed external auditory meatus 1 opened by opening the open tube 143, 144.

The technical spirit of automatically measuring the air pressure difference using the speaker 110 and the microphone 120 may be applied to various fields. In an example of a related-art in-ear earphone, when worn, positive pressure is generated in the external auditory meatus, possibly causing damage to sound quality or the ear. Thus, by combining the air pressure adjustment apparatus 100, 100' to adjust the air pressure, equilibrium state of the eardrum may be maintained to avoid damage to sound quality and the ear. By combining the air pressure adjustment apparatus 100, 100' with a hearing aid to adjust air pressure inside the ear of a user, a phenomenon of howling or feedback, occlusion effect, or the like, to a user may be reduced. The air pressure adjustment apparatus 100, 100' may be utilized as an equipment for tympanometry.

According to various embodiments, air pressure difference may be automatically adjusted by measuring an air pressure difference between the inside of the mid ear and the air pressure of the external auditory meatus. Accordingly, inconvenience to a user due to an air pressure difference of the ear may be overcome, and convenience to a user may be improved.

Various embodiments may be implemented as software that includes instructions stored in machine-readable storage media readable by a machine (e.g., a computer). A device may call instructions from a storage medium and that is operable in accordance with the called instructions, including the air pressure adjustment apparatus 100 and 100'.

When the instructions are executed by a processor, the processor may perform a function corresponding to the instructions directly or by using other components under the control of the processor. The instructions may include a code generated by a compiler or a code executable by an interpreter. A machine-readable storage medium may be provided in the form of a non-transitory storage medium. Herein, the term "non-transitory" only denotes that a storage medium does not include a signal but is tangible, and does not distinguish the case in which data is semi-permanently stored in a storage medium from the case in which data is temporarily stored in a storage medium.

According to an embodiment, the method according to the above-described embodiments may be provided as being included in a computer program product. The computer program product may be traded as a product between a seller and a consumer. The computer program product may be distributed online in the form of machine-readable storage media (e.g., compact disc read only memory (CD-ROM)) or through an application store (e.g., Play Store™ and App Store™) or distributed online (e.g., downloaded or uploaded) directly between to users (e.g., smartphones). In the case of online distribution, at least a portion of the computer program product may be at least temporarily stored or temporarily generated in a server of the manufacturer, a server of the application store, or a machine-readable storage medium such as memory of a relay server.

According to embodiments of the disclosure, the respective elements (e.g., module or program) of the elements mentioned above may include a single entity or a plurality of entities. Furthermore, at least one element or operation from among the corresponding elements mentioned above may be omitted, or at least one other element or operation may be added. Alternatively or additionally, a plurality of components (e.g., module or program) may be combined to form a single entity. As such, the integrated entity may perform functions of at least one function of an element of each of the plurality of elements in the same manner as or in a similar manner to that performed by the corresponding element from among the plurality of elements before integration. The module, a program module, or operations executed by other elements according to variety of embodiments may be executed consecutively, in parallel, repeatedly, or heuristically, or at least some operations may be executed according to a different order, may be omitted, or the other operation may be added thereto.

Although the disclosure has been described by way of examples, it will be understood by those skilled in the art that various changes in form and details may be made therein without departing from the essential characteristics thereof. In addition, the embodiments according to the disclosure are not intended to limit the technical spirit of the disclosure, but to describe the technical aspect and the scope of the technical aspect of the disclosure is not limited by the embodiments herein. Accordingly, the scope of protection of the disclosure should be construed by the following claims, and all technical ideas that fall within the scope of the disclosure are to be construed as falling within the scope of the disclosure.

What is claimed is:

1. An air pressure adjustment apparatus, comprising:
a speaker;
a microphone;
an earplug of which a main body comprises an elastic material so as to seal an external auditory meatus, based on the earplug being worn on an ear of a user, and which comprises an air pressure adjustment part penetrating the main body;
an air pressure adjustment device configured to adjust a fluid volume of the air pressure adjustment part; and
a processor configured to:
output a sound through the speaker based on the earplug being worn,
measure the air pressure difference between air pressure of an internal part of the middle ear and air pressure of an external auditory meatus on the basis of strength of a received echo based on an echo of the sound reflected from the eardrum of the user being received through the microphone, and
adjust the air pressure difference by moving the air pressure adjustment device according to the measured air pressure difference,
wherein the processor is configured to adjust a moving speed of the air pressure adjustment device according to a change speed corresponding to one profile selected from a plurality of profiles associated with a change speed of the fluid volume of the air pressure adjustment part.

2. The air pressure adjustment apparatus of claim 1, further comprising:
an air pressure sensor configured to sense the air pressure of the external auditory meatus,
wherein the processor is configured to, based on receiving the echo from the microphone, determine the air pressure of the internal part of the middle ear on the basis of data relating to the echo strength according to the air pressure of the internal part of the middle ear, and measure an air pressure difference between the air pressure of the internal part of the middle ear and the air pressure of the external auditory meatus by sensing the air pressure of the external auditory meatus through the air pressure sensor.

3. The air pressure adjustment apparatus of claim 1, wherein the processor is configured to:
calculate a change amount of the fluid volume of the air pressure adjustment part corresponding to the air pressure difference, and
adjust the air pressure difference by moving the air pressure adjustment device so that the fluid volume of the air pressure adjustment part changes according to the calculated change amount.

4. The air pressure adjustment apparatus of claim 1, wherein the processor is configured to:
based on the middle ear internal air pressure being higher than the air pressure of the external auditory meatus, move the air pressure adjustment device so that the fluid volume of the air pressure adjustment part decreases, and
based on the middle ear internal air pressure of the internal part of the middle ear being lower than the air pressure of the external auditory meatus, move the air pressure adjustment device so that the fluid volume of the air pressure adjustment part increases.

5. The air pressure adjustment apparatus of claim 1, wherein the processor is configured to adjust a moving speed of the air pressure adjustment device based on an air pressure adjustment plan inside an airplane according to a flight plan of the airplane.

6. The air pressure adjustment apparatus of claim 1, wherein the processor is configured to, based on an air pressure difference with a sign opposite to an air pressure difference that is a reference of the adjustment being measured while moving the air pressure adjustment device in one direction along the air pressure adjustment part to adjust the air pressure difference, move the air pressure adjustment device in a direction opposite to the one direction.

7. The air pressure adjustment apparatus of claim 1, wherein the main body or the air pressure adjustment device further comprises:
an open tube configured to be openable for opening the external auditory meatus sealed according to wearing of the earplug,
wherein the processor is configured to, while adjusting the air pressure difference by moving the air pressure adjustment device in a direction along the air pressure adjustment part, based on an air pressure difference having a sign opposite to a sign of the air pressure difference that is a reference of the adjustment being measured, open the sealed external auditory meatus by opening the open tube.

8. The air pressure adjustment apparatus of claim 1, wherein the processor is configured to, based on the air pressure difference not being adjusted according to moving of the air pressure adjustment device, output a notification indicating that the external auditory meatus is not sealed.

9. A method for adjusting an air pressure of an air pressure adjustment apparatus including a speaker, a microphone, an earplug of which a main body comprises an elastic material so as to seal an external auditory meatus, based on the earplug being worn on the ear of a user, and which comprises an air pressure adjustment part penetrating the main body, the method comprising:
outputting a sound through the speaker based on the earplug being worn;
measuring the air pressure difference between air pressure of an internal part of the middle ear and air pressure of an external auditory meatus on the basis of strength of a received echo based on an echo of the sound reflected from the eardrum of the user being received through the microphone; and
adjusting the air pressure difference by moving the air pressure adjustment device according to the measured air pressure difference,
wherein the adjusting comprises adjusting a moving speed of the air pressure adjustment device according to a change speed corresponding to one profile selected from a plurality of profiles associated with a change speed of the fluid volume of the air pressure adjustment part.

10. The method of claim 9, wherein the air pressure adjustment apparatus further comprises:
an air pressure sensor configured to sense the air pressure of the external auditory meatus, and
wherein the measuring comprises:
determining air pressure of the internal part of the middle ear on the basis of data relating to the echo strength according to the air pressure of the internal part of the middle ear; and
sensing the air pressure of the external auditory meatus through the air pressure sensor.

11. The method of claim 9, wherein the adjusting comprises:
 calculating a change amount of the fluid volume of the air pressure adjustment part corresponding to the measured air pressure difference; and
 moving the air pressure adjustment device so that the fluid volume of the air pressure adjustment part changes according to the calculated change amount.

12. The method of claim 9, wherein the adjusting comprises, based on the air pressure of the internal part of the middle ear being higher than the air pressure of the external auditory meatus, moving the air pressure adjustment device so that the fluid volume of the air pressure adjustment part decreases, and based on the air pressure of the internal part of the middle ear being lower than the air pressure of the external auditory meatus, moving the air pressure adjustment device so that the fluid volume of the air pressure adjustment part increases.

13. The method of claim 9, wherein the adjusting comprises adjusting a moving speed of the air pressure adjustment device based on an air pressure adjustment plan inside an airplane according to a flight plan of the airplane.

\* \* \* \* \*